United States Patent [19]

Cobia

[11] Patent Number: Plant 6,046

[45] Date of Patent: Oct. 27, 1987

[54] CACTACEAE PLANT

[75] Inventor: Barnell L. Cobia, Winter Garden, Fla.

[73] Assignee: B. L. Cobia, Inc., Winter Garden, Fla.

[21] Appl. No.: 740,116

[22] Filed: May 30, 1985

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new plant variety which is sterile and produces a light or pastel salmon colored bloom, in comparison to the 'Christmas Cheer' variety has a faster growth rate, larger specimens at comparable stages of maturity and a more upright posture and compact appearance as evidenced by more erect stems and heavier branching with or without inducement by pruning. The new variety has a greater resistance to stem breakage and longer and wider phylloclades when the 'Christmas Cheer' variety. It also has a greater resistance to nutrient deficiencies and known problem diseases of the related varieties. It has a greater tendency for multiple bud formations and a greater resistance to bud abscission than the 'Christmas Cheer' variety. It also has a habit or producing more blooms that have longer tepals than those of the 'Christmas Cheer' variety and a longer bloom life. The bloom in color is distinguishable from the 'Christmas Cheer' variety by having a generally lighter appearing color and a color that is dominated by yellowish pink and/or orange hues and are more uniformly distributed throughout the marginal and center field areas of the tepal blades of the tube laminating and tube forming series of tepals when compared to the 'Christmas Cheer' variety.

4 Drawing Figures

The invention relates to a new and distinct plant variety of the Cactaceae family and which has been named the *Zygocactus truncatus* 'Christmas Fantasy' by the inventor.

Certain plant varieties of the Cactaceae family are well known in the foliage plant market and among these are the varieties of the *truncatus* species of Zygocactus genus which are commonly referred to as "Christmas Cacti" for they tend to bloom in the months of November and December in the Northern Hemisphere and hence appear in the retail market area primarily during the Thanskgiving and Christmas seasons.

Among the various *Zygocactus truncatus* varieties are the 'Christmas Cheer' and 'Peach Parfait' varieties. Both of these varieties are fertile plants with blooms that are generally considered "salmon" colored but which are nevertheless distinguishable. The variety known as 'Christmas Cheer' has a bloom life in the area of about 5 to about 8 days but the stems of the variety tend to droop so that the variety lacks the upright appearance considered by many purchasers as evidencing a healthy plant specimen. The 'Peach Parfait' variety is a descendant of the 'Christmas Cheer' variety and exhibits many improved characteristics over its antecedant and which are pointed out in U.S. Plant Pat. No. 3,693. The variety has a bloom life which is comparable to that of the 'Christmas Cheer' variety and the bloom color is dominated by pink, red and/or reddish orange hues that are mainly concentrated in the marginal blade areas of the tepals.

A general object of the invention has been to develop a sterile variety of the Cactaceae family which would produce a light or pastel salmon colored bloom that would be distinguishable from known related varieties and have an acceptable bloom life for marketing purposes. Once particular objective has been to develop a sterile variety with a salmon bloom color that is distinguishable from that of the 'Christmas Cheer' and 'Peach Parfait' varieties and which has a generally longer bloom life in comparison to these varieties. Other objectives have been to develop a sterile variety which is productive of a light or pastel salmon colored bloom that is distinguishable from that of the 'Christmas Cheer' and 'Peach Parfait' varieties and which as a plant is capable of withstanding a greater amount of handling without stem breakage than is exhibited by such varieties.

The objects of the invention have been fully realized by the development of the new plant variety hereinafter described in detail. The new plant variety was developed in a nursery located at Winter Garden, Fla., as a hybrid secured by cross pollinating the flower of a plant specimen of an unnamed research variety that is a descendant of the 'Kris Kringle' variety (see U.S. Plant Pat. No. 3,688) with pollen from a plant specimen of another unnamed research variety. The seeds taken from the fertilized seed pod were cultivated at the mentioned nursery location and after prolonged observation of the seedlings, the hybridized plant of the new plant variety was selected and asexually reproduced by the inventor at the Winter Garden nursery by the propagation of stem cuttings taken from the original hybrid plant. The maternal and paternal plant varieties are both research varieties that have not appeared in the market area.

Through successive propagations, it has been ascertained that specimens of the new plant variety are distinguishable from specimens of the parent varieties and other related varieties known to the inventor by a growth habit which is evident in plant specimens propagated and grown under nursery conditions utilized in the growing of tropical plants at Winter Garden, Fla., as combining the following principal characteristics:

1. A faster growth rate and thus larger specimens at comparable stages of maturity than its parent or either of the 'Christmas Cheer' or 'Peach Parfait' varieties.

2. A more upright posture and compact appearance than the 'Christmas Cheer' variety as evidenced by more erect stems and heavier (more frequent) branching with or without inducement by pruning.

3. A greater resistance to stem breakage from handling than either of the 'Christmas Cheer' or 'Peach Parfait' varieties.

4. Phylloclades that are longer and wider in comparison to its parents and the 'Christmas Cheer' variety.

5. A greater resistance to nutrient deficiencies and to known problem diseases of the related varieties, such as Pythium and damp-off fungii than the 'Christmas Cheer' variety.

6. A greater tendency for multiple bud formations at the tips of the branches, and a greater resistance to bud abscission than its maternal parent or the 'Christmas Cheer' variety.

7. A habit of producing more blooms than its maternal parent or the 'Christmas Cheer' variety and which are larger than those of the paternal parent and have longer tepals than those of the 'Christmas Cheer' variety.

8. A bloom life (7-10 days) that is generally longer than the bloom life (5-8 days) of the 'Christmas Cheer' and 'Peach Parfait' varieties.

9. A bloom that in color is distinguishable from those of the 'Christmas Cheer' and 'Peach Parfait' varieties by (a) a generally lighter appearing color than either of the 'Christmas Cheer' of 'Peach Parfait' varieties, and (b) a color that is dominated by yellowish pink and/or orange hues and more uniformly distributed throughout the marginal and center field areas of the tepal blades of the tube laminating and tube forming series of tepals in comparison to either of the 'Christmas Cheer' or 'Peach Parfait' varieties.

10. Sterile specimens.

The accompanying drawings serve by color photography to illustrate the new plant variety and wherein one sheet photographically illustrates a potted 20 month old plant specimen that was propagated in March, pruned to 2 tiers above the propagated stem cutting in August of the year of propagation and thereafter in July of the following year again pruned to the third tier above the propagated stem cutting. Another sheet photographically illustrates various buds at the tips of certain branches of a specimen of the new variety. A third sheet photographically illustrates a typical bloom of the new plant variety while a fourth sheet photographically illustrates the bloom as generally seen along the axis of the perianth tube.

The following is a detailed description of the new plant variety with colors and hues, unless otherwise clearly indicated by the text through the absence of color notations, being named in accord with the ISCC-NBS Method of Designating Colors, (U.S. Dept. of Commerce, National Bureau of Standards, Circular 553, issued Nov. 1, 1955) the named colors being interpreted from color notations derived by comparison with the color specimens in the "Neighboring Hues Edition" of the Munsell Book of Color, published by the Munsell Color Company, Inc., of Baltimore, Md. The description is further based on observations of well fertilized plants of less than two years of age from initial propagation and which were grown under 50-75% shaded glasshouse nursery conditions in the Winter Garden, Fla. area and wherein temperatures range from about 60° F. to about 85° F. during the winter months, from about 75° F. to about 95° F. during the summer months, and are ambient during the intervening periods.

DETAILED PLANT DESCRIPTION

I. Name: *Zygocactus truncatus* 'Christmas Fantasy'.

II. Parentage:

A. *Maternal.*—ZH1178-T, an unnamed research variety which in comparison to the new plant variety is a slower grower with a less erect posture and less resistance to breakage during handling. It also has smaller phylloclades that are both narrower in width and shorter in length. In addition the maternal variety matures less blooms, has a greater tendency for bud abscission and develops generally white tepals.

B. *Paternal.*—ZH6658, an unnamed research variety which in comparison to the new plant variety is a slower grower with greater natural branching characteristics and a very compact growth habit. It also has phylloclades that are smaller both in width and length. In addition, it has small blooms that have a deeper salmon color.

III. Classification:

A. *Botanic.*—(Britton and Rose, *The Cactaceae,* Constable and Co., Ltd., London 1937, Vol. IV). (1) Family: Cactaceae. (2) Tribe: Cereeae. (3) Sub-tribe: Epiphyllanae. (4) Genus: Zygocactus. (5) Species: *truncatus* (Haworth) Schumann.

B. *Commercial.*—Thanksgiving-Christmas blooming cactus.

IV. Form: Epiphyllic and terrestrial, shade loving, succulent, leafless plant with jointed and branched stems.

V. Stems:

A. *General.*—Irregular with usually multichotomous branching of both upright and pendulous, adventitiously rootable, flattened phylloclades that have a prominent midrib and prominently toothed lateral wings.

B. *Phylloclades.*—(1) General: Elongated and flat with a transversely elongated, areole bearing, truncated apex, with inwardly tapering basal wing margins that merge with a usually broadly pointed basal juncture with the phylloclade therebelow, and with an axially located areole usually being associated with each tooth. (2) Midrib: (a) General — Extends longitudinally of phylloclade and continuously through joints and with a laterally tapering cortex at the wing insertions. Pith surrounding vascular bundles that branch and provide lateral extensions of the vascular system to the marginal teeth. (b) Texture — Smooth, waxy epidermis with wax in small embedded scales and becoming woody in basal stem areas with specimen aging. (c) Size (at maturity) — 1. Length: Usually between 30 and 70 mm. and averaging about 48 mm. 2. Thickness: Usually between 2 and 14 mm. and averaging about 4.0 mm. (d) Color (at maturity) — Usually dark yellowish green (10 GY 3/4) and/or moderate olive green (7.5 GY 4/6) (7.5 GY 3/4) (7.5 GY 4/4). (3) Wings: (a) General — Dentate and generally flattened from midrib cortex to tooth insertions and with slight thinning taper toward margins. (b) Margins — Toothed. (c) Texture — Succulent to leathery with smooth, waxy epidermis where the wax is arranged in small embedded scales of higher density than in midrib area, and becoming corky in the basal stem areas with specimen aging. (d) Size (at maturity) — 1. Thickness: About 1–2 mm. in the area intermediate the margin and midrib. 2. Width: Usually 10–18 mm. as measured from phylloclade axis to most offset lateral areole and averaging about 14.7 mm. 3. Color (at maturity): Usually dark yellowish green (10 GY 4/4) (10 GY 3/4) (10 GY 4/6) and/or moderate olive green (7.5 GY 4/6) (7.5 GY 3/4) (7.5 GY 4/4). (4) Teeth: (a) Shape — 1. General: Generally flattened and tapered along the margins from the wing insertion to an apex having a hyaline, single cell, pointed spine with non-predictable bending. 2. Adaxial margin: Usually straight to concave. 3. Abaxial margin: Usually straight to convex. (b) Orientation — Usually project distally of phylloclade in an opposite to alternate arrangement. (c) Margins — Entire. (d) Texture — Succulent to leathery with smooth waxy epidermis having wax in small embedded scales of density comparable to wings, and becoming corky in basal stem areas with specimen aging. (e) Size (at maturity) — 1. Thickness: Usually 1–1.5 mm. in center area. 2. Areole to apex dimensions (adaxial marginal side): Usually 6–13 mm. in the upper quadrants of the phylloclades. (f) Number — Usually 4–7 per phylloclade. (g) Color — Usually dark yellow green (10 GY 4/4) (10 GY 3/4) (10 GY 4/6 ) and/or moderate olive green (7.5 GY 4/6) (7.5 GY3/4) (7.5 GY 4/4). (5) Areoles: (a) Terminal areole — Large, elongated, oval shaped with several acicular bristles, and several buds that may mature into either new phylloclades or flowers. The opposite ends of the aerole ard located adjacent to subsidiary areoles which are in turn located at the axils of the teeth at the distal end of the phylloclade. (b) Axillary aeroles — Acicular bristles without glochidia but having copious, short, brownish, multicellular, wooly hairs. In areoles located below the teeth at the distal end of the phylloclade, there is sometimes one areole which is frequently latent.

VI. Buds: Unarmored, ovoid and chorophyllous.

VII. Flowers:

A. *General.*—Sessile, zygomorphic, commonly solitary, terminal, perfect and epigynous with double hypanthium and whorled tepals (undifferentiated sepals and petals) having a spiral emergence as a perianth provided with a sepaloid series of free tepals, a tube laminating series of tepals, and a tube forming series of united tepals.

B. *Sepaloid series.*—(1) General: Free tepals inserted on top of ovary. (2) Shape: Deltoid in outer members of whorl and grading inwardly in the whorl to provide progressively greater length dimensions and broader apices. All members have a pointed tip and entire margins with sparse irregular teeth appearing mainly in the apex areas of the inner members of the whorl. (3) Texture: Succulent and glabrous outer whorl members and grading inwardly in whorl to silken blades with fleshy basal areas. (4) Number: Usually 4–5. (5) Size (at full bloom): (a) Length (base-tip dimension) — Usually less than 10 mm. (b) Width (maximum) — Usually less than 9 mm. (6) Color (at full bloom); The tepal members have marginal blade areas that in color are dominated by purplish pink and/or pink hues that merge with a distally extending color in the basal area that is dominated by a yellow green hue. Commonly pale purplish pink (7.5 RP 8/4), light purplish pink (5 RP 8/6), light pink (near 10 RP 8/4) and/or moderate pink (near 10 RP 8/4) in marginal areas and light yellow green (2.5 GY 8/4) (2.5 GY 8/6) (5 GY 8/5) in the basal areas of outer whorl members. (7) Orientation: Usually erect at full bloom.

C. *Tube laminating series.*—(1) General: Tepals inserted on ovary and basally united below the throat as outer laminations on the perianth tube and with progressively greater amount of basal fusion inwardly in the whorl. (2) Shape: Zygomorphic and grading inwardly in the whorl with progressively greater length dimensions and broader apices so that the blade area changes inwardly in the whorl from ovate with an acute tip to spatulate with a broader acute tip. Entire margins with sparse, irregular teeth mainly in apex areas. (3) Texture: Succulent and glabrous outer whorl members and grading inwardly to silken blades with slightly fleshy basal areas. (4) Number: Usually 7–10 tepals. (5) Size (at full bloom): (a) Length (base-tip dimension) — Usually ranging from about 30 to about 45 mm. (b) Width (maximum) — Usually ranging from about 10 to about 16 mm. (6) Color (at full bloom): (a) General — Tepals with basal areas that are translucent white and marginal and center field blade areas that in color are dominated by a yellowish pink hue which merges with the distally extending basal area color. (b) Basal area — Usually translucent white at insertion and along tube attached area. (c) Blade area — Usually moderate yellowish pink (10 R 7/6) and/or strong yellowish pink (10 R 7/8) (10 R 7/10) in the marginal and center field blade areas. (7) Orientation: Usually acute to perpendicular at full bloom.

D. *Tube forming series.*—(1) General: Tepals basally united to form hollow perianth tube that is inserted on ovary and equipped at its throat with an irregular carina (keel). (2) Shape: (a) Perianth tube — Elongated and ellipsoidal in cross section with the major ellipsoidal axis usually generally normal to the plane of the supporting phylloclade. (b) Blades — Nearly zygomorphic and thinly spatulate with acute tips and entire margins having sparse irregular teeth in apex areas. (c) Carina (keel) — Irregular and transcending. (3) Texture: (a) Perianth tube — Thick, succulent and slightly ribbed. (b) Blades — Translucent and silken. (c) Carina (keel) — Fleshy. (4) Number: Usually 8–9. (5) Size (at full bloom): (a) Perianth tube — 1. Length (base-keel): Usually 32–38 mm. along tube axis. 2. Major axis: Usually 5–7 mm. at throat interior. 3. Minor axis: Usually 5–6 mm. at throat interior. (b) Blades — 1. Length (keel-tip): Usually 32–37 mm. 2. Width (maximum): Usually 12–15 mm. (6) Color (at full bloom): (a) Perianth tube — A basic field that is translucent white with longitudinally extending, randomly arranged striations or streaks. Commonly purplish white (5 RP 9/1) and/or pinkish white (5 R 9/1) in basic field area and deep purplish pink (5 RP 6/10) in streaks. (b) Blades — Marginal and center field blade areas that are dominated by yellowish pink and/or orange hues and merging with a translucent white in the basal area. Commonly moderate yellowish pink (near 5 YR 8/4), light yellowish pink (near 5 YR 8/4) and/or moderate orange (2.5 YR 7/8) in marginal and center field blade areas. (c) Carina (keel) — Color dominated by a purplish red hue. Commonly moderate purplish red (10 RP 5/10) and/or strong purplish red (10 RP 5/12). (7) Orientation: Acute to recurve.

E. *Androecium* (*stamens*).—(1) General: Numerous exserted and diadelphous stamens with one group having filaments basally fused to the perianth tube and the other group having filaments basally united to form a nectary housing, thin annulus around the style and which is provided with thin, deflexed, irregular, toothed margin or ruffle at the throat of the annulus. (2) Stamen number: (a) Tube attached group — Usually 64–86. (b) Basally united group — Usually 18–21. (3) Filaments: (a) General — Translucent with anther connective. (b) Shape — Long, slender, terete. (c) Texture — Glabrous and capillaceous. (d) Color — Translucent white. (e) Size (at full bloom) — 1. Length: (a) Tube attached group — Usually between 53 and 63 mm. (b) Basally united group — Usually between 47 and 53 mm. 2. Diameter: Usually about 0.75 mm. at insertion and tapering to about 0.50 mm. at distal end. (4) Anthers: (a) General — Adnate with four longitudinally dehiscent pollen sacs and connective inserted at end. (b) Shape — Elongated. (c) Texture — Waxy. (d) Color (before dehiscence) — Dominated by a greenish yellow hue. Commonly pale greenish yellow (10 Y 9/4). (e) Sterility — Sterile.

F. *Gynoecium* (*pistil*).—(1)General: Exserted with compound, pariental placentation and united style surrounded by annular diffuse yellowish nectary at its insertion. (2) Style: (a) General — Stout and inserted at ovary. (b) Shape — Elongated and terete. (c) Texture — Fleshy and smooth. (d) Color — Dominated by a purplish pink and/or purplish red hue. Commonly moderate purplish red (5 RP 5/10), deep purplish pink (5 RP 6/10) and/or strong purplish red (5 RP 5/12). (e) Size (at full bloom) — 1. Length: Usually 58 to 67 mm. 2. Diameter: Usually 1=1.5 mm intermediate opposite ends. (3) Stigma; (a) General — Exserted and erect with usually 6–8 inner marginally adhering lobes. (b) Shape — Elongated and tapering toward lobe tips and having relatively blunt apices. (c) Texture — Fleshy and smooth with inner sides of lobes having short glutinous capillaceous hairs. (d) Color — Dominated by a purplish red hue. Commonly moderate purplish red (7.5 RP 4/8) (10 RP 5/10) and/or strong purplish red (5 RP 5/12). (e) Size — 1. Length: Usually 5–7 mm. along inner margins. (4) Ovary: (a) General — Inferior with thin epidermis and usually 6–7 carpules with numerous ovules. (b) Shape — Terete to ovoid and generally broadening from insertion to floral end. Slightly ribbed single concavity with inserted style. (c) Texture — Succulent with glabrous thin outer epidermis. (d) Color — Usually moderate yellow green (2.5 GY 6/6) (5 GY 6/6) (5 GY 5/6) and/or strong yellow green (2.5 GY 6/8) (2.5 GY 7/8). (e) Size — 1. Length: Usually 9–12 mm. from insertion to cavity base. 2. Major axis: Usually 7–10 mm. at top end of concavity.

VIII. Growth habit: The specimens of the new variety are sterile and they have a faster growth rate which is productive of larger specimens at comparable stages of maturity than either of the parents or either of the 'Christmas Cheer' or 'Peach Parfait' varieties. The new plant variety also has a more upright posture and compact appearance than the 'Christmas Cheer' variety and this is seen by reference to the more erect stems and heavier (more frequent) branching. The new variety has a greater tendency to branch with or without inducement by pruning than the 'Christmas Cheer' variety and in comparison to this variety and the 'Peach Parfait' variety, it also has a greater resistance to stem breakage from handling. The phylloclades of the new variety are longer and wider than the parental or 'Christmas Cheer' varieties. It also has a greater resistance to nutrient deficiencies and to known problem diseases of the related varieties, such as Pythium and damp-off fungii than the 'Christmas Cheer' variety.

The new variety has a greater tendency for multiple bud formations at the tips of the branches and a greater resistance to bud abscission than its maternal parent or the 'Christmas Cheer' variety. It also has a habit of producing more blooms than its maternal parent or the 'Christmas Cheer' variety, and these blooms are larger than those of the paternal parent and have longer tepals than those of the 'Christmas Cheer' variety. The bloom life of the new variety extends from about 7 to about 10 days in comparison to a bloom life of from about 5 to 8 days for the 'Christmas Cheer' and 'Peach Parfait' varieties. The bloom color of the new variety is distinguishable by a generally lighter appearing color than either of the 'Christmas Cheer' or 'Peach Parfait' varieties and it is dominated by a yellowish pink and/or orange hues and more uniformly distributed throughout the marginal and center field areas of the tepal blades of the tube laminating and tube forming series of tepals when compared to either of the 'Christmas Cheer' or 'Peach Parfait' varieties The following is a general description of a specimen of the new plant variety which was grown from the propagation of a single phylloclade at the nursery in Winter Garden, Fla.

Age of plant: 20 months from initial propagation of a single phylloclade. The specimen was pruned to the second tier above the propagated phylloclade during the 6th month and thereafter to the third tier above the propagated phylloclade during the 17th month following propagation.

Branches from propagated phylloclade: 2.

Total numer of new phylloclades remaining on specimens: 95.

General:

| Branch No. | No. of Phylloclades | Max. Length | No. of Tips |
|---|---|---|---|
| 1 | 37 | 65 mm. | 12 |
| 2 | 58 | 70 mm. | 20 |

Midribs:

| Branch No. | Length (avg.) | Thickness (avg.) |
|---|---|---|
| 1 | 49.8 mm. | 4.1 mm. |
| 2 | 47.6 mm. | 3.7 mm. |

Wings:

| Branch No. | Center Thickness (avg.) | Max. Width (avg.) |
|---|---|---|
| 1 | 1.5 mm. | 13.24 mm. |
| 2 | 1.5 mm. | 13.60 mm. |

Teeth:

| Branch No. | No. per Phylloclade (avg.) | Center Thickness (avg.) | Areole to Apex Length (avg.) |
|---|---|---|---|
| 1 | 5.5 | 1.0 mm. | 9.4 mm. |
| 2 | 5.7 | 1.0 mm. | 9.3 mm. |

Phylloclade color: Moderate olive green (7.5 GY 4/6) and/or dark yellowish green (10 GY 3/4).

The following is a general description of a flower of the new plant variety and which bloomed in December on a 20 month old plant specimen grown under shaded glasshouse nursery conditions in Winter Garden, Fla.

No. of buds and blooms on plant specimen: 61.
Bloom life: 8 days.
Sepaloid series of tepals:

*Number.*—5.

*Size (at full bloom).*—Maximum base-tip dimension: 10 mm. Minimum base-tip dimension: 2 mm. Maximum width dimension: 9 mm.

*Color (at full bloom).*—Pale purplish pink (7.5 RP 8/4), light pink (near 10 RP 8/4), moderate pink (10 RP 8/4) and/or light purplish pink (5 RP 8/6) in continuous field of outer whorl members of small tepals. Light yellow green (2.5 GY 8/6) and/or brilliant yellow green (5 GY 8/6) in marginal and center field areas and light yellow green (2.5 GY 8/6) and/or brilliant yellow green (5 GY 8/6) in the basal areas of the inner whorl members.

Tube laminating series of tepals:

*Number.*—9.

*Size (at full bloom).*—Maximum base-tip dimension: 45 mm. Minimum base-tip dimension: 30 mm. Maximum blade width: 16 mm. Minimum blade width: 10 mm.

*Color.*—Moderate yellowish pink (10 R 7/6) and/or strong yellowish pink (10 R 7/8) in marginal and center field areas of the blades and gradually fading to translucent white in the basal areas of the blades.

Tube forming series of tepals:

*Number.*—9.

*Size (at full bloom).*—Perianth tube: Length (base to keel) — 36 mm. along tube axis. Major axis — 6–8 mm. at throat interior. Minor axis — 5–7 mm. at throat interior. Blades: Maximum length (keel-tip) — 37 mm. Minimum length (keel-tip) — 32 mm. Maximum blade width — 13 mm. Minimum blade width — 10 mm.

*Color.*—Perianth tube: A major field of pinkish white (5 R 9/1) with random striations of deep purplish pink (5 RP 6/10). Blades: Moderate yellowish pink (near 5YR 8/4), light yellowish pink (near 5 YR 8/4), moderate orange (2.5 YR 7/8) and/or light yellowish pink (near 5 YR 8/4) in marginal and center field areas of the blades and translucent white in proximity of keel.

Androecium:

*Stamen number.*—Tube attached group: 64–84. Basally united group: 18–21.

*Filaments.*—Color: Translucent white in basal area and translucent white in distal area. Size (at full bloom): Length — Tube attached group: 56 mm. (avg.). Basally united group: 50 mm. (avg.). Diameter: About 0.50 mm. intermediate the opposite ends.

*Anthers.*—Color (before dehiscing): Pale greenish yellow (10 Y 9/4).

Gynoecium (pistil):

*Style.*—Color: Moderate purplish red (5 RP 5/10) and/or strong purplish red (5 RP 5/12) in basal area and strong purplish red (5 RP 5/12) in distal area. Size (at full bloom): Length — 58–67 mm. Diameter — 1.0–1.5 mm. intermediate the opposite ends.

*Stigma.*—Color: Moderate purplish red (7.5 RP 4/8) and/or strong purplish red (5 RP 5/12). Size: 6 mm. (avg.) lobe length.

*Ovary.*—Color: Moderate yellow green (2.5 GY 6/6) and/or strong yellow green (2.5 GY 7/8). Size (at full bloom): Major axis — 9–12 mm. at distal end of concavity. Minor axis — 2–3 mm. at distal end of concavity.

I claim:

1. The new and distinct plant variety of the Cactacea family and described and illustrated and which is principally distinguished by a growth habit that combines the following characteristics:

(1) A faster growth rate providing larger specimens at comparable stages of maturity than either of the 'Christmas Cheer' or 'Peach Parfait' varieties, (2) A more upright posture and compact appearance than the 'Christmas Cheer' variety as evidenced by more erect stems and heavier (more frequent) branching with or without inducement by pruning, (3) A greater resistance to stem breakage from handling than either of the 'Christmas Cheer' or 'Peach Parfait' varieties, (4) Phylloclades that are longer and wider in comparison to the 'Christmas Cheer' variety, (5) A greater resistance to nutrient deficiences and to known problem diseases of the related varieties than the 'Christmas Cheer' variety, (6) A greater tendency for multiple bud formations at the tips of the branches and a greater resistance to bud abscission than the 'Christmas Cheer' variety, (7) A habit of producing more blooms than the 'Christmas Cheer' variety and which are larger and have longer tepals than those of the 'Christmas Cheer' variety, (8) A bloom life that is generally longer than the bloom life of the 'Christmas Cheer' and 'Peach Parfait' varieties, (9) A bloom that in color is distinguishable from those of the 'Christmas Cheer' and 'Peach Parfait' varieties by (a) a generally lighter appearing color than either of the 'Christmas Cheer' or 'Peach Parfait' varieties, and (b) a color that is dominated by yellowish pink and/or orange hues and more uniformly distributed throughout the marginal and center field areas of the tepal blades of the tube laminating and tube forming series of tepals in comparison to either of the 'Christmas Cheer' or 'Peach Parfait' varieties, and

(10) Sterile specimens.

* * * * *

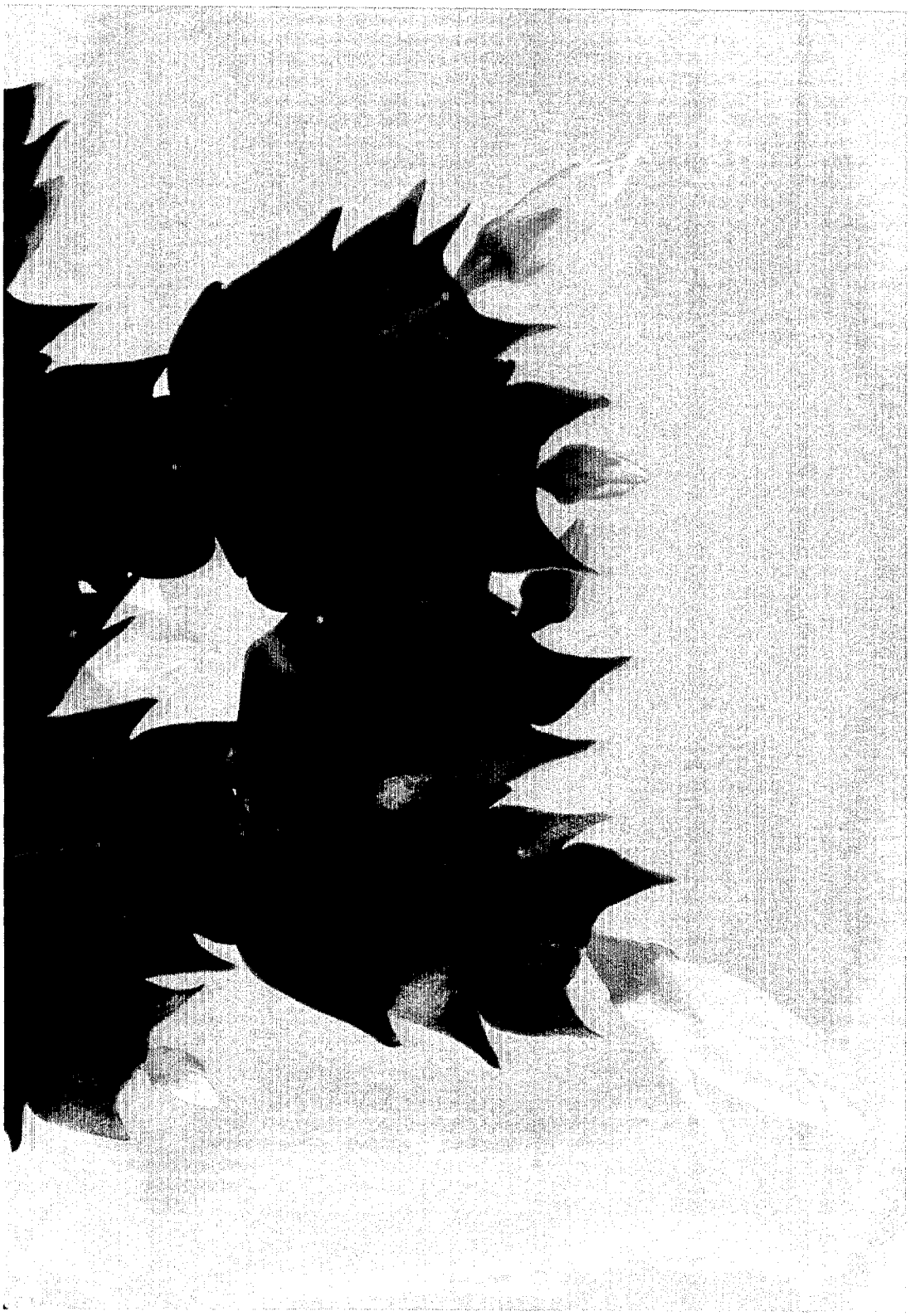

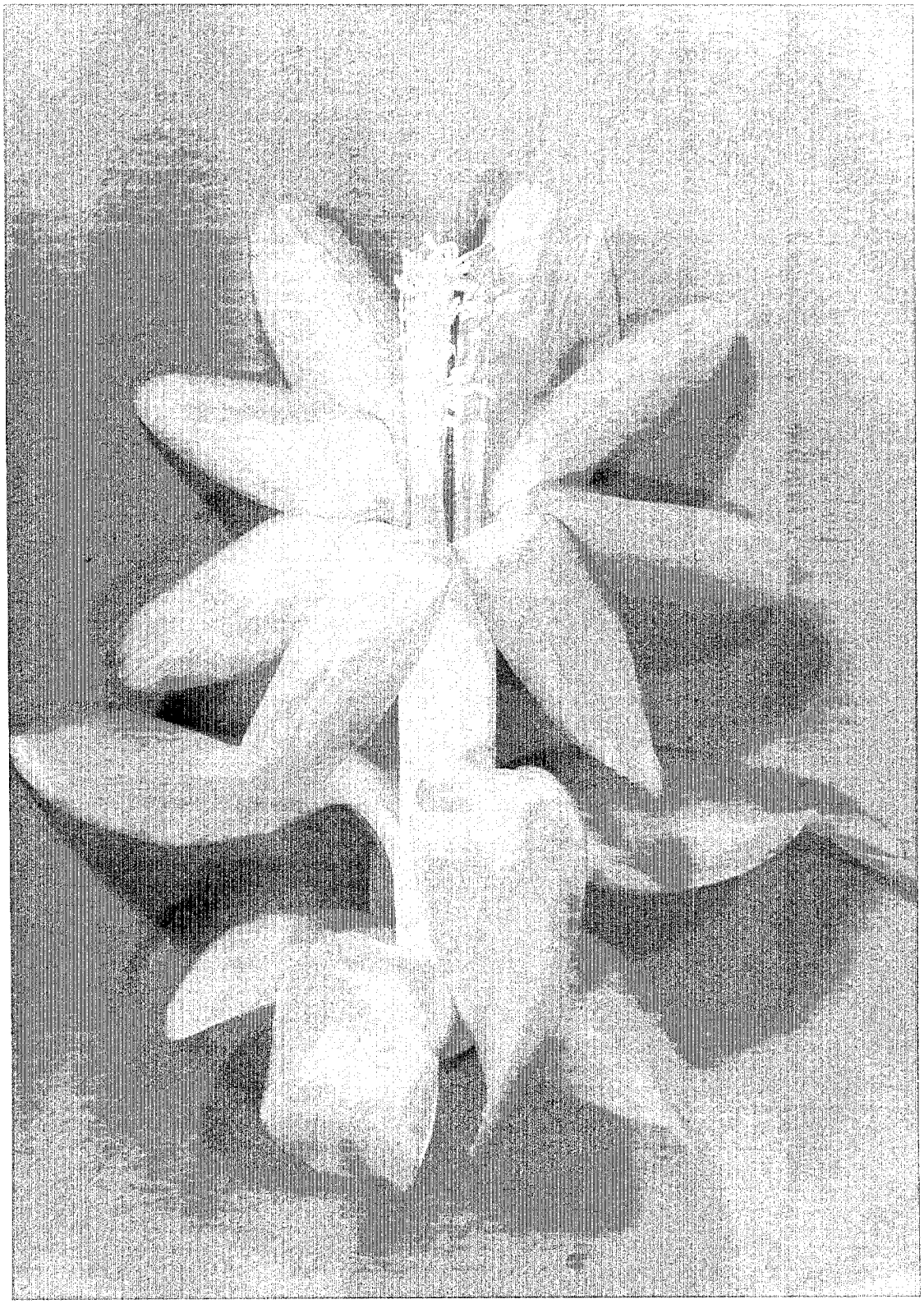

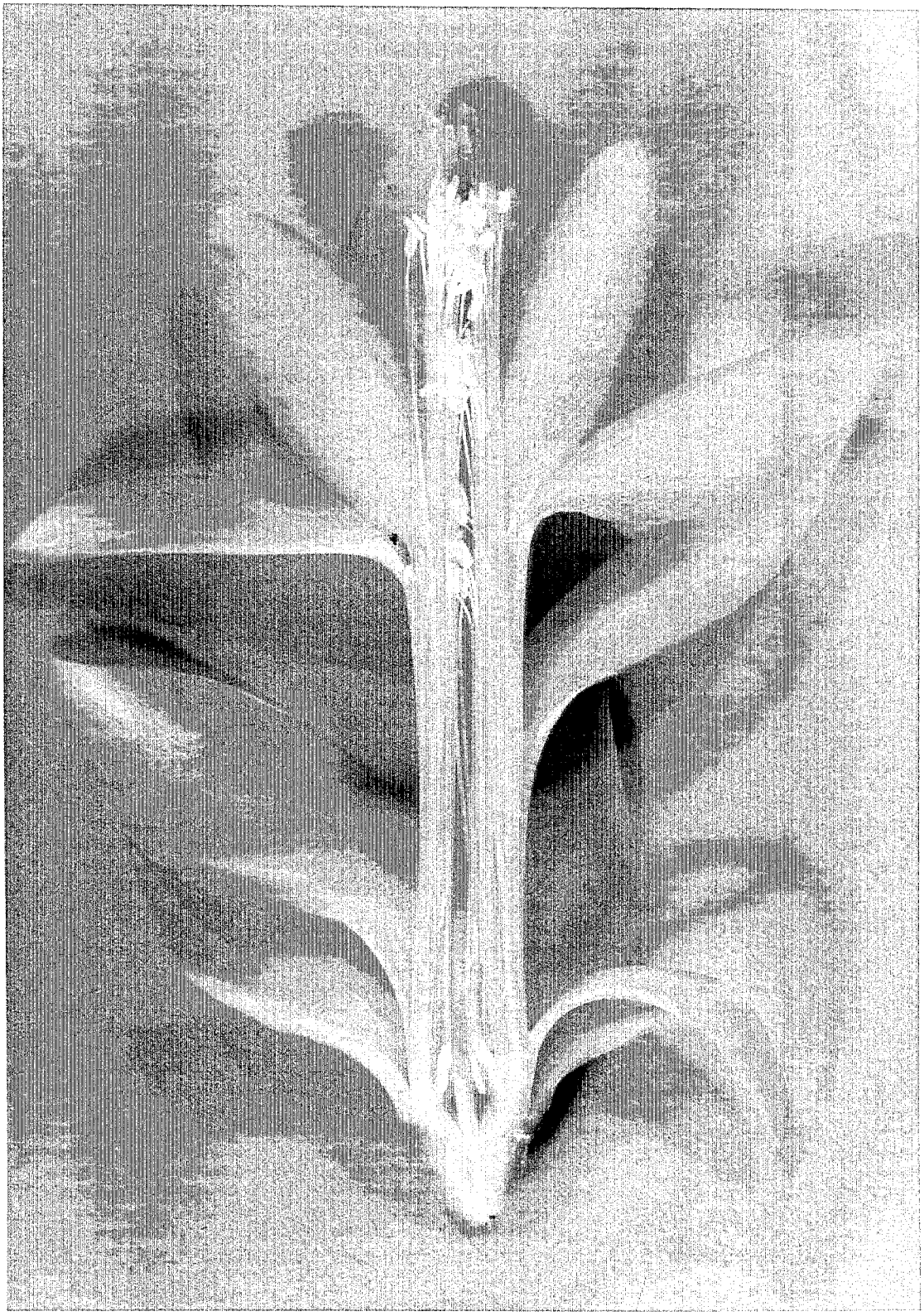

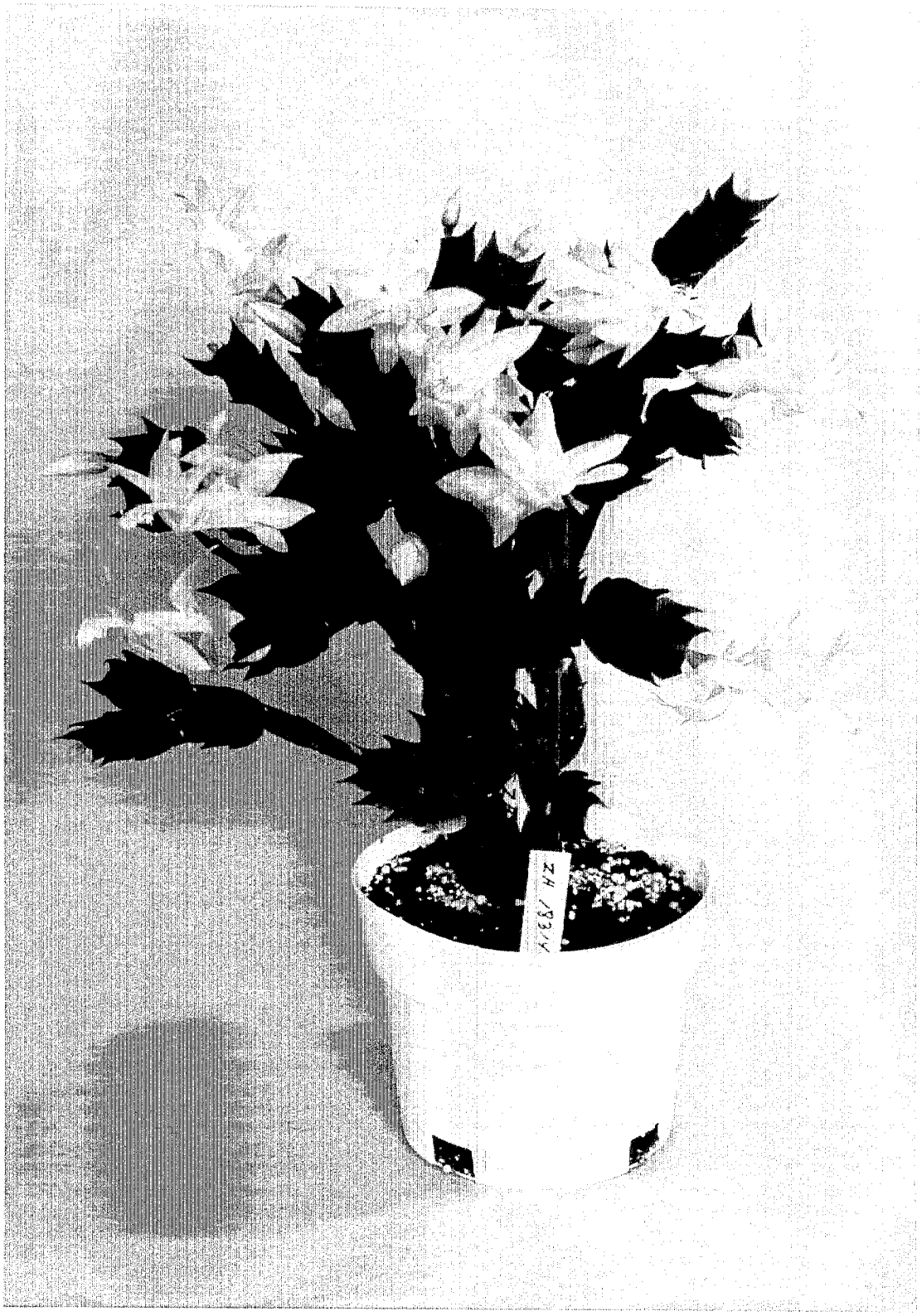
ZH 1831